United States Patent [19]

Nishino

[11] Patent Number: 5,656,669

[45] Date of Patent: Aug. 12, 1997

[54] RESTORATIVE NEUROPHARMACOLOGICAL AGENT FOR MOTOR AND SPEECH DISTURBANCE

[75] Inventor: Katsuhiro Nishino, Akita, Japan

[73] Assignee: Sumitomo Pharmaceuticals Co., Ltd., Osaka, Japan

[21] Appl. No.: 317,392

[22] Filed: Oct. 4, 1994

[30] Foreign Application Priority Data

Jul. 5, 1994 [JP] Japan ................... 6-177444

[51] Int. Cl.$^6$ ................... A61K 31/195; A61K 31/165
[52] U.S. Cl. ................... 514/567; 514/565; 514/614
[58] Field of Search ................... 514/567, 565, 514/614

[56] References Cited

U.S. PATENT DOCUMENTS

| | | | |
|---|---|---|---|
| 4,497,826 | 2/1985 | Narabayashi et al. | 514/567 |
| 4,690,949 | 9/1987 | Yoshida et al. | 514/561 |

OTHER PUBLICATIONS

Dennis M. Feeny et al, "Amphetamine, Haloperidol, and Experience Interact to Affect Rate of Recovery After Motor Cortex Injury", Science, vol. 217, 27 Aug., 1982, pp. 855–857.

Davis et al, "Amphetamine and Physical Therapy Facilitate Recovery of Function from Stroke: Correlative Animal and Human Studies", Cerebral Diseases, Fifteenth Research (Princeton) Conference, 1987.

Ueno et al., "The Effect of L–threo–DOPS . . . ", Abstracts of 29th Annual Meeting of Japanese Neurological Society, May 25–27, 1988.

Saito et al., "Observation of Remarkable Effect . . . ", Abstracts of 11th Annual Meeting of the Japanese Neurotherapy Society, May 12–13, 1993.

Nishino et al., "1–threo DOPS . . . ", Japanese Journal of Cerebral Blood Flow and Metabolism, vol. 5, No. 1, 1993.

Nishino et al., "Neurobehavioral Study . . . ", Functional Neurosurgery, vol. 30, 1991.

Nishino et al., "Facilitation Effect of . . . ", Abstracts of the 19th Annual Meeting of the Japanese Stroke Society, Mar. 10–11, 1994.

Primary Examiner—Phyllis G. Spivack
Attorney, Agent, or Firm—Sughrue, Mion, Zinn, Macpeak & Seas

[57] ABSTRACT

A restorative neuropharmacological method of treating motor or speech disturbance comprising administration of L- or DL-threo-DOPS or its pharmaceutically acceptable acid-addition-salt to a patient is provided by stimulating the central nervous system so as to enhance intrinsic neuroplasticity and thus increasing functional compensation.

14 Claims, No Drawings

RESTORATIVE NEUROPHARMACOLOGICAL AGENT FOR MOTOR AND SPEECH DISTURBANCE

CROSS-REFERENCE TO RELATED APPLICATION

This application claims priority benefits under 35 U.S. C Section 119 of Japanese Patent application No. 6-177444, filed Jul. 5th, 1994, the entire disclosure of which is incorporated herein by reference.

BACKGROUND OF THE INVENTION

1. Field of the Invention

This invention relates to a restorative neuropharmacological agent for motor and speech disturbance originating from central nervous system disorders.

2. Description of Related Art

L-threo-DOPS (Droxidopa) is a central norepinephrine precursor and is known as an active ingredient for norepinephrine activated nerve function improving agents. Clinically, L-threo-DOPS is used to improve impotent feet and orthostatic dizziness in Parkinson's disease (stage 3 in the degree of severity according to Yahr) and also to improve orthostatic hypotension, syncope and orthostatic dizziness in familial amyloid polyneuropathy or Shy-Drager Syndrome.

Conventionally, improvement of motor and speech disturbance originating from central nervous system disorders has been difficult to treat, and the development of a therapeutic agent was generally believed to be impossible.

SUMMARY OF THE INVENTION

The object of this invention is to provide restoration from motor and speech disturbance originating from central nervous system disorders by stimulating the central nervous system and thus increasing functional compensation based on intrinsic plasticity of the central nervous system, which restoration conventional physical therapy alone cannot provide.

In order to achieve the object set forth above, the restorative neurological therapeutic agent for motor and speech disturbance according to this invention contains L-threo-DOPS as an active ingredient.

L-threo-DOPS (Droxidopa) is (−)-(2R, 3R)-2-amino-3-hydroxy-3-(3, 4-dihydroxyphenyl) propionic acid (according to the JAN nomenclature) or (−)-threo-3-(3, 4-dihydroxyphenyl) L-serine (according to the INN nomenclature), the structural formula of which is shown below.

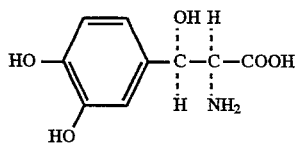

L-threo-DOPS, whose molecular formula is $C_9H_{11}NO_5$, is white or light brown crystals or crystalline powder with no taste or odor. Droxidopa dissolves only slightly in water, and dissolves very little in ether, ethanol and glacial acetic acid. It is difficult to measure a clear melting point or decomposition point for L-threo-DOPS. L-threo-DOPS shows some changes when the temperature is raised to the vicinity of 220° C., starts melting at 225° C., and turns into a black liquid at around 230° C. The pKa of L-threo-DOPS is 7.88, measured by the titration method. DL-threo-DOPS, which contains 50% L-threo-DOPS, can also be used in this invention. Hereafter, L-threo-DOPS and DL-threo-DOPS are generically denoted as "threo-DOPS".

In this invention, threo-DOPS can be used in a pharmaceutically acceptable acid-addition-salt form as well. For example, inorganic acids such as hydrochloric acid, hydrobromic acid and sulfuric acid and organic acids such as fumaric acid, citric acid, tartaric acid and succinic acid can be used to form an acid-addition-salt.

Threo-DOPS can be manufactured by conventional methods, such as those described in U.S. Pat. No. 4,562,263 and U.S. Pat. No. 4,480,109.

Conventional pharmacological features of threo-DOPS are as follows: (1) it is directly converted to 1-norepinephrine by the action of the aromatic L-amino acid decarboxylase which is widely distributed in a living body, and thus has an effect of replenishing norepinephrine, (2) it passes through the blood-brain barrier into the brain, (3) it specifically recovers norepinephrine activated nerve functions which have decreased in the central and peripheral nervous system, and (4) it shows various actions via the adrenaline receptors in various tissues. The restorative neuropharmacological agent for motor and speech disturbance according to this invention is effective in improving motor paralysis and motor aphasia after stroke due to subarachnoid hemorrhage, brain infarction, brain hemorrhage, etc. or post-traumatic brain injury wherein physical therapy alone cannot provide improvement, and is particularly effective in increasing the recovery rate in acute stroke cases and enhanced recovery in certain chronic stroke cases. Such actions of threo-DOPS have not been brought to light before, and there has been no functional improvement agent which shows such actions.

The functional improvement agent which has threo-DOPS as an active ingredient can be in any form including capsules, tablets, confection, pills, parvule, suppository, solution and ampules. The functional improvement agent which has threo-DOPS as an active ingredient can contain fillers, expanders, binders, dissolution retardants, surfactants, adsorbents, lubricants, coloring agents, perfumes, preservatives, etc. Such preparations can be manufactured following a conventional method. This unique functional improvement agent can also contain other pharmaceutically active ingredients as well. A conventional norepinephrine activated nerve function improving agent which has L-threo-DOPS as an active ingredient is commercially available under the name "DOPS" (manufactured and distributed in Japan by Sumitomo Pharmaceuticals Company, Limited).

In particular, the restorative neuropharmacological agent for motor and speech disturbance according to this invention should preferably be used together with a peripheral decarboxylase inhibitor such as benserazide (hereafter referred to as "BSZ") or carbidopa to promote transfer of threo-DOPS into the brain. To use them together, separate preparations of threo-DOPS and of a peripheral decarboxylase inhibitor can be administered either at the same time or at different times, or a mixture of them can be administered. BSZ can be manufactured using a conventional method.

For the administration method of the restorative neuropharmacological agent for motor and speech disturbance according to this invention, depending on the form it takes, oral administration, rectal administration, nasal administration, intravenous administration, hypodermic administration, intramuscular administration, etc. are possible, of which oral administration is preferable.

The amount of oral administration of the restorative neuropharmacological agent according to this invention is 60–1,200 mg droxidopa for common adults per day, preferably 100–900 mg, and more preferably 100–400 mg. When a peripheral decarboxylase inhibitor is also administered, the amount of the peripheral decarboxylase inhibitor is empirically 1–10% of the amount of droxidopa, preferably 2.5–7.5%, and more preferably about 5%. For example 5% is particularly preferable for BSZ. However, depending on the age, weight, symptoms, and past history etc. of the subject to whom the medication is administered, the amount of administration of droxidopa and the peripheral decarboxylase inhibitor can be changed as appropriate. In clinical examples, administration of droxidopa alone has shown sufficient efficacy.

DETAILED DESCRIPTION OF THE PREFERRED EMBODIMENTS

Preparations according to this invention are described below by referring to examples, However, this invention is not limited to those examples.

EXAMPLE 1

Preparing Capsules 200 weight parts of droxidopa, 167 weight parts of an excipient and 3 weight parts of a lubricant are homogeneously mixed, and empty capsules are filled with this mixture in such a way that each capsule contains 200 mg of droxidopa. A capsule preparation is thus obtained.

EXAMPLE 2

Preparing Capsules 100 weight parts of droxidopa, 168 weight parts of an excipient and 2 weight parts of a lubricant are homogeneously mixed, and empty capsules are filled with this mixture in such a way that each capsule contains 100 mg of droxidopa. A capsule preparation is thus obtained.

The excipient for Examples 1 and 2 described above is chosen from among lactose, white sugar, glucose, D-mannitol, potato starch, corn starch, wheat starch, calcium carbonate, calcium sulfate, anhydrous calcium phosphate, sodium bicarbonate, crystalline cellulose, a mixture of these, etc. The lubricant is chosen from among magnesium stearate, calcium stearate, talc, etc.

Clinical testing was conducted to evaluate the effects of the restorative neuropharmacological agent for motor and speech disturbance according to this invention.

Clinical subjects for motor disturbance were 2 cases after cerebral aneurysm operations (subarachnoid hemorrhage), 9 cases of brain hemorrhage and 10 cases of brain infarction with chronic apoplectic paralysis, i.e. a total of 21 cases (12 males and 9 females, age 43–83 with an average 61.9±2.5 years). For these clinical subjects, the average time elapsed from the onset had occurred was 100 days, Table 1 shows the 21 clinical subject cases and 6 control cases.

TABLE 1

List of the short term administration testing cases

| Case No. | Age | Sex | Diagnosis* | Improvement in FMS |
|---|---|---|---|---|
| Cases administered L-DOPS | | | | |
| 1 | 43 | Female | BH | Improved |
| 2 | 51 | Female | BI | Improved |
| 3 | 50 | Male | BH | Improved |
| 4 | 57 | Female | BI | Improved |
| 5 | 59 | Male | BH | Improved |
| 6 | 64 | Female | BI | No change |
| 7 | 66 | Female | SAH | Improved |
| 8 | 47 | Male | BH | No change |
| 9 | 51 | Male | SAH | Improved |
| 10 | 61 | Male | BI | No change |
| 11 | 60 | Male | BI | Improved |
| 12 | 62 | Female | BH | Improved |
| 13 | 57 | Male | BH | No change |
| 14 | 76 | Male | BI | Improved |
| 15 | 64 | Male | BI | Improved |
| 16 | 64 | Female | BH | Improved |
| 17 | 83 | Male | BI | Improved |
| 18 | 71 | Female | BH | Improved |
| 19 | 73 | Male | BI | No change |
| 20 | 75 | Male | BI | No change |
| 21 | 52 | Female | BH | Improved |
| Control cases (not administered L-DOPS) | | | | |
| 1 | 46 | Male | BH | No change |
| 2 | 62 | Male | BI | No change |
| 3 | 71 | Female | BH | No change |
| 4 | 70 | Male | BI | Improved |
| 5 | 68 | Female | BI | No change |
| 6 | 76 | Male | BI | No change |

*BH: Brain hemorrhage
BI: Brain infarction
SAH: Subarachnoid hemorrhage

First, the clinical subjects received physical therapy without administration of droxidopa (L-DOPS), and then they were evaluated with FMS (Fugl-Meyer score), 10-meter walking and the Barthel index. The clinical subjects then received administration of 300 mg droxidopa (L-DOPS) per day for 2 days in addition to the physical therapy, and were evaluated with FMS. 10-meter walking and with the Barthel index.

As a result, of the 21 cases to whom droxidopa was administered, 15 cases showed improved FMS, i.e. FMS increased by 2.5±0.5, which was higher than zero, 1±0.2, for the control cases. The t-test showed that P was less than 0.005, indicating a significant difference. For this FMS, 10 of the 21 cases showed improvement in upper limb motor function, 6 of the 21 cases showed improvement in lower limb motor function, and 3 of the 21 cases showed improved balance. On the other hand, of the 6 control cases without droxidopa administration, 0 case, 1 case and 0 case, respectively, showed such improvement.

All of the 12 cases with central-facial palsy showed improvement. On the other hand, none of 6 control cases showed improvement. 19 cases of the 21 cases showed improvement in the 10-meter walking. Of these, one case showed improvement in the Barthel index, i.e. improvement in ADL (activities of daily living).

After 1–2 weeks, droxidopa was administered again for 2 consecutive days to 5 of the 15 cases who had showed improvement in FMS of the 21 cases who had received 2 days of administration, and further improvement was observed for 3 cases. This indicates that more improvement in motor functions can be expected by administering droxidopa over a longer period of time. The administration of droxidopa to the clinical subjects was then halted, but the level of the improvement effect on motor functions was maintained.

Based on the above results, low term administration testing was conducted. The clinical subjects were 10 neurological stable cases who had an onset of stroke 2 months to 2 years before the testing, and 200–500 mg/day of droxidopa was administered for 2 weeks to 2 months. As a result, 7 cases showed improvement in the Barthel index, i.e. improvement in ADL (activities of daily living) was observed for 7 cases of the 10 cases. The results were independent of the time elapsed since onset of the illness. Table 2 shows the list of the 10 clinical subject cases.

that more improvement in speech disturbance can be expected by administering droxidopa for a long period of time.

Administration of droxidopa to these clinical subjects was stopped after 2 weeks. As a result, speech was totally lost in 2 cases. Subsequently, administration of droxidopa was stopped twice and, in one case, speech was totally lost every time administration was stopped and restored when administration was resumed. This indicates that there is a close relationship between speech improvement and administration of droxidopa. No serious side-effect was observed in the clinical subjects.

Droxidopa has already been commercially available in Japan, and the following is reported regarding its safety.

(A) Acute toxicity (LD50) is shown in Table 3.

TABLE 2

List of the long term administration testing cases

| Case No. | Age | Sex | Diagnosis | Improvement in ADL | Amount of L-DOPS administered per day × duration |
|---|---|---|---|---|---|
| 1 | 43 | Female | Brain stem infarction | Improved | 200 mg × 2W |
| 2 | 51 | Female | Subarachnoid hemorrhage | No change | 200 mg × 2W |
| 3 | 50 | Female | Brain hemmorrhage | Improved | 300 mg × 3W |
| 4 | 57 | Male | Subarachnoid hemorrhage + Brain infarction | No change | 200 mg × 4W |
| 5 | 59 | Female | Brain hemorrhage | Improved | 200 mg × 2W |
| 6 | 64 | Male | Brain hemorrhage | Improved | 200 mg × 8W |
| 7 | 66 | Male | Brain hemorrhage (AVM) | Improved | 500 mg × 6W |
| 8 | 47 | Male | Brain hemorrhage | Improved | 300 mg × 6W |
| 9 | 51 | Male | Brain hemorrhage | Improved | 200 mg × 2W |
| 10 | 61 | Female | Subarachnoid hemorrhage | No change | 300 mg × 7W |

AVM: Arteriovenous malformation

The clinical subjects for speech disturbance were 10 cases of Broca aphasia after stroke (3 males and 7 females, age 51–65 with an average of 58.6±1.6 years).

First, without administration of droxidopa, the clinical subjects were evaluated with standard aphasia testing (SLAT). After 300 mg of droxidopa was administered to the clinical subjects 3 times a day for 2 days, speech improved.

TABLE 3

Acute toxicity results (LD50, mg/kg)

| Administration via | Mice, ICR strain | | Rats, SD strain | | beagle dogs | | rhesus monkeys | |
|---|---|---|---|---|---|---|---|---|
| | Male | Female | Male | Female | Male | Female | Male | Female |
| Oral | >10000 | >10000 | >10000 | >10000 | >5000 | >5000 | >5000 | >5000 |
| Hypodermic | >10000 | >10000 | 84 | 95 | — | — | — | — |
| Intravenous | >100 | >100 | 16–19 | 19 | — | — | — | — |

For 8 of the clinical subjects, 100 mg of droxidopa was administered once a day for a subsequent 2 weeks and evaluation was conducted using SLAT.

After 2 weeks of droxidopa administration, the average improvement rates based on SLAT were as follows: "hearing" (short sentences, 33%; imperatives, 16%, "reading" (short sentences, 20%; Chinese character words, 10%), "speaking" (names, 27%; actions, 13%), "writing" (Japanese syllabary words, 20%), and "repeating" (10%). 8 of the 10 cases showed improved SLAT results after 2 weeks of administration. That is, one case showed improvement in "hearing", 3 cases in "reading", 7 cases in "speaking", 6 cases in "writing" and 2 cases in "repeating". This indicates As for general symptoms, reduced voluntary motions, deep breathing and bradypnea were observed with mice and rats, but no abnormal symptom was observed with dogs and rhesus monkeys.

(B) Subacute toxicity testing 60, 300, 1,500 mg/kg/day was orally administered to SD rats, 200, 600, 2,000 mg/kg/day was orally administered to beagle dogs, and 300, 1,000, 3,000 mg/kg/day was orally administered to rhesus monkeys consecutively for 3 months. As a result, for dogs and monkeys, no abnormality was observed in various observations and testing evaluations. For the rats, suppressed voluntary motions, necrosis of kidney uriniferous tubuli, necrosis of cardiac muscles, etc.

were observed with 60 mg/kg/day and higher. Suppression of weight increases and such were observed with 300 mg/kg/day and higher. Drooling was observed with 1,500 mg/kg/day.

(C) Chronic toxicity testing 10, 30, 100, 300 mg/kg/day was orally administered to SD rats, and 125, 500, 2,000 mg/kg/day was orally administered to beagle dogs consecutively for 12 months. As a result, for dogs, no abnormality was observed in various observations and testing evaluations. For the rats, suppression of weight increases, an increase in thymus weight, necrosis of kidney uriniferous tubuli, degeneration of kidney glomeruli, etc. were observed with 30 mg/kg/day and higher, and drooling, myocarditis and calcification of cardiac muscles, etc. were observed with 100 mg/kg/day and higher.

(D) Procreation testing (1) Pre-pregnancy and early pregnancy administration testing 60, 200, 600 mg/kg/day was orally administered to SD rats (male and female) consecutively. As a result, no influence was observed on the mating rate, conception rate, nidation number, embryo/neonate death, teratogenic actions or fetal development.

(2) Organ forming period administration testing 60, 200, 600 mg/kg/day was orally administered to SD rats consecutively. As a result, lower body weights of fetuses and an increase in the occurrence of undulating ribs were observed with 200 mg/kg or higher. However, they were within the range in which they can be restored after birth. No other influence was observed. 30, 100, 300 mg/kg/day was orally administered to rabbits consecutively. As a result, no influence on the rabbits was observed.

(3) Perinatal and lactation period administration testing 60, 200, 600 mg/kg/day was orally administered to SD rats consecutively. As a result, shortening of the pregnancy period was observed with 600 mg/kg, and suppression of neonatal development after birth was observed with 60 mg/kg or higher. No other influence was observed.

(E) Antigenicity testing

Endodermoreaction, systemic anaphylaxis reaction, PCA reaction and intra-gel sedimentation reaction testing on guinea pigs (Hartley strain, male) yielded negative results.

(F) Mutagenicity testing

Back mutation testing using microorganisms, chromosome abnormality testing using cultured cells and micronucleus testing on mice were conducted and no mutagenicity was observed.

It is understood that although the present invention has been described in detail with respect to preferred embodiments thereof, various other embodiments and variations are possible to those skilled on the art which fall within the scope and spirit of the invention, and such other embodiments and variations are intended to be covered by the following claims.

What is claimed is:

1. A method of treating motor paralysis or motor aphasia, due to stroke or post-traumatic brain injury, said method comprising administration of a pharmaceutically effective amount of L- or DL-threo-DOPS or a pharmaceutically acceptable acid-addition-salt thereof to a patient.

2. A method of treating motor paralysis or motor aphasia, due to stroke caused by subarachnoid hemorrhage, brain infarction or brain hemorrhage, or post-traumatic brain injury, said method comprising administration of a pharmaceutically effective amount of L- or DL-threo-DOPS or a pharmaceutically acceptable acid-addition-salt thereof to a patient.

3. A method of treating motor aphasia comprising administration of a pharmaceutically effective amount of L- or DL-threo-DOPS or a pharmaceutically acceptable acid-addition-salt thereof to a patient.

4. A method as described in claim 1, 2 or 3 comprising administration of a mixture of a peripheral decarboxylase inhibitor and L- or DL-threo-DOPS or a pharmaceutically acceptable acid-addition-salt thereof.

5. A method as described in claim 1, 2 or 3 comprising administration of a preparation containing L- or DL-threo-DOPS or a pharmaceutically acceptable acid-addition-salt thereof and a preparation containing a peripheral decarboxylase inhibitor, said preparations being administered either separately or simultaneously.

6. A method as described in claim 1, 2 or 3 comprising administration of a mixture of a peripheral decarboxylase inhibitor, which is benserazide or carbidopa, and L- or DL-threo-DOPS or a pharmaceutically acceptable acid-addition-salt thereof.

7. A method as described in claim 1, 2 or 3 comprising administration of a preparation containing L- or DL-threo-DOPS or a pharmaceutically acceptable acid-addition-salt thereof and a preparation containing a peripheral decarboxylase inhibitor, which is benserazide or carbidopa, said preparations being administered either separately or simultaneously.

8. A method of treating motor paralysis or motor aphasia, due to stroke or post-traumatic brain injury, said method comprising administration of a pharmaceutically effective amount of L-threo-DOPS or a pharmaceutically acceptable acid-addition-salt thereof to a patient.

9. A method of treating motor paralysis or motor aphasia, due to stroke caused by subarachnoid hemorrhage, brain infarction or brain hemorrhage, or post-traumatic brain injury, said method comprising administration of a pharmaceutically effective amount of L-threo-DOPS or a pharmaceutically acceptable acid-addition-salt thereof to a patient.

10. A method of treating motor aphasia comprising administration of a pharmaceutically effective amount of L-threo-DOPS or a pharmaceutically acceptable acid-addition-salt thereof to a patient.

11. A method as described in claim 8, 9 or 10 comprising administration of a mixture of a peripheral decarboxylase inhibitor and L-threo-DOPS or a pharmaceutically acceptable acid-addition-salt thereof.

12. A method as described in claim 8, 9 or 10 comprising administration of a preparation containing L-threo-DOPS or a pharmaceutically acceptable acid-addition-salt thereof and a preparation containing a peripheral decarboxylase inhibitor, said preparations being administered either separately or simultaneously.

13. A method as described in claim 8, 9 or 10 comprising administration of a mixture of a peripheral decarboxylase inhibitor, which is benserazide or carbidopa, and L-threo-DOPS or a pharmaceutically acceptable acid-addition-salt thereof.

14. A method as described in claim 8, 9 or 10 comprising administration of a preparation containing L-threo-DOPS or a pharmaceutically acceptable acid-addition-salt thereof and a preparation containing a peripheral decarboxylase inhibitor, which is benserazide or carbidopa, said preparations being administered either separately or simultaneously.

* * * * *